United States Patent [19]

Butler

[11] 4,128,336

[45] Dec. 5, 1978

[54] SPECTROSCOPIC APPARATUS AND METHOD

[75] Inventor: Louis R. P. Butler, Pretoria, South Africa

[73] Assignee: The South African Inventions Development Corporation, South Africa

[21] Appl. No.: 714,313

[22] Filed: Aug. 16, 1976

[30] Foreign Application Priority Data

Aug. 21, 1975 [ZA] South Africa .................. 75/5358
Aug. 21, 1975 [ZA] South Africa .................. 75/5359

[51] Int. Cl.² .............................................. G01J 3/30
[52] U.S. Cl. .................................... 356/307; 313/210; 356/314
[58] Field of Search ................................... 356/85–87, 356/82

[56] References Cited

U.S. PATENT DOCUMENTS 3,489,942 1/1970 Walsh et al. .................. 356/85 X
3,644,045 2/1972 Walsh .............................. 356/85

*Primary Examiner*—F. L. Evans
*Attorney, Agent, or Firm*—Fitch, Even, Tabin & Luedeka

[57] ABSTRACT

This invention relates to an apparatus and a method for spectroscopically analyzing substances, by fluorescent or resonant detection. An atomic cloud of a reference element is generated by cathodic sputtering and irradiated with radiation emitted from a substance of unknown composition. Generation of the atomic cloud is ceased and the inherent radiation of the atomic cloud allowed to decay. Any fluorescent or resonant radiation of the atomic cloud is then detected to determine the presence or concentration of the reference element in the unknown substance. Further, the amount of background radiation is detected by determining the amount of radiation extant when the concentration of atoms in the atomic cloud has decreased to substantially zero. The invention also provides an abnormal glow discharge lamp having two or more windows, the lamp being particularly suitable for use with the apparatus. The lamp further has a hollow anode with a transverse planar cathode.

15 Claims, 7 Drawing Figures

SPECTROSCOPIC APPARATUS AND METHOD

BACKGROUND OF THE INVENTION

This invention relates to a spectroscopic apparatus and method. More particularly, the invention relates to a glow discharge lamp and to an apparatus and a method for spectroscopically analysing substances by means of fluorescence detection.

Glow discharge lamps, having a hollow, tubular anode and a planar, transverse cathode, are known to the applicant. These known lamps generate spectral radiation by creating an excited atomic cloud by cathodic sputtering, and are utilised as primary sources of radiation. It is a feature of these lamps that, as they are intended to be only primary radiation sources, they have only one window such that generated radiation is emitted from the lamp in only one direction.

Such known glow discharge lamps may be used to analyse an unknown substance by absorption or fluorescence spectroscopy techniques. With these techniques, the unknown substance is stimulated so that it emits primary radiation characteristic of its component elements, and this primary radiation is passed through an atomic cloud of a particular reference element, the presence and concentration of which in the unknown substance is to be determined. The atoms of the atomic cloud then selectively absorb components of the primary radiation and are caused to fluoresce emitting secondary radiation characteristic of the atoms of the atomic cloud. The absorption or the fluorescence is then detected in order to determine whether or not the reference element is included in the unknown substance. With fluorescence spectroscopy, the excited atoms of the atomic cloud may re-emit radiation of the same wavelength as that absorbed by the atoms, such re-radiation being termed "resonance radiation". Alternatively radiation of a larger wavelength may be re-radiated. An apparatus and a method for detecting resonance radiation is described in British Pat. No. 1,042,129 granted to the Commonwealth Scientific and Industrial Research Organisation.

It is thus often required that an atomic cloud be generated such that radiation from the external source may pass through the cloud, e.g. in absorption spectroscopy; or, e.g. with fluorescence spectroscopy, that the atomic cloud be illuminable by primary radiation from the external source, and that secondary radiation of the cloud be emitted along a path that is transverse to that of the primary radiation.

Instead of the atomic cloud being generated by cathodic sputtering it may be generated by thermal means, although cathodic sputtering is the preferred manner. However, when the cloud is generated by cathodic sputtering the atoms are sufficiently excited to emit inherent radiation, which is of a broad bandwidth that detracts from the accuracy and sensitivity of detection.

It has been found that with an atomic cloud generated by cathodic sputtering in a suitable lamp the intensity of inherent radiation decays much more rapidly than the concentration of neutral atoms. The concentration of neutral atoms has been found to obey the equation $$N(t) = N_0\, e^{-k(P)t}$$

where $N(t)$ is the number density of atoms at time t, $N_0$ is the number density of atoms at time $t = 0$, and $k(P)$ is a rate constant that is a function of the pressure P extant in the lamp.

The rate constant has been found to be inversely related to the pressure P whereas the decay time of radiation emitted by the atomic cloud is substantially independent of the pressure. Thus, conditions may be obtained in which the atomic cloud still has a substantial concentration even though its inherent radiation is substantially zero, by suitably pressurizing the lamp in which the atomic cloud is generated.

SUMMARY OF THE INVENTION

Thus, according to a first aspect of the invention there is provided a glow discharge lamp which includes
a housing, having at least two windows;
a hollow anode within the housing, the anode being open at both ends; and
a cathode located within the housing and having a planar discharge surface located transversely to, and spaced from, an end of the anode; and
connecting means for connecting the anode and the cathode to an electricity supply source.

The glow discharge lamp may have an anode-cathode separation that is sufficiently small for an abnormal glow discharge to occur. Further the cathode may have a restricted discharge area.

If the housing has only two windows, they may be disposed on the same optical axis that is transverse to the axis of the anode. Alternatively, they may be disposed on different transverse optical axes. If the housing has more than two windows, one may be disposed on the axis of the anode and the others may be disposed on further axes that are transverse to the axis of the anode. The optical axis of each of the windows of the housing may pass through that region of the lamp where, in use, an atomic cloud is generated by electrical excitation of the anode and the cathode.

Thus the anode may have an axial length sufficiently small for the atomic cloud, or a part thereof, to be located beyond the end of the anode remote from the cathode, each optical axis may then pass through this region beyond the end of the anode. Alternatively, the anode may also have one or more windows opposite the region where the atomic cloud is generated, these anode windows being disposed on an axis or axes transverse to the axis of the anode.

The anode may be tubular in form and the cathode may extend around an end portion of the anode, adjacent the planar cathode surface.

In order to facilitate changing of the reference element, the cathode may comprise two parts, an annular part secured to the housing and a replaceable disc-shaped part, that is of the reference element, being replaceably secured to the annular part.

The windows of the housing may be of any suitable material, e.g. quartz or lithium fluoride.

In order to be able to control the atmosphere in the housing, it may be gas tight and it may have an inlet opening and an outlet opening through which a suitable gas may be introduced into and removed from within the housing. This gas may be an inert gas, such as argon.

According to a second aspect of the invention there is provided an apparatus for spectroscopically determining the presence of a particular element in a substance of unknown composition including
generating means for generating by cathodic sputtering an atomic cloud of the particular element, the generating means being such that the atomic cloud may be irradiated by source radiation emitted from the substance;

detection means for detecting the amount of radiation emitted by the atomic cloud; and enabling means for enabling the detection means after the generating means has ceased generating the atomic cloud and when the atomic cloud no longer emits inherent radiation.

The generating means may preferably comprise a glow discharge lamp in accordance with the first aspect of the invention.

The enabling means may comprise a mechanical shutter that is displaceable in and out of the optical path between the generating means and the detection means. Alternatively, the detection means may be electrically operable, the enabling means also being electrically operable. With such electrically operable enabling means it may be adapted to electrically ground the output of the detection means thereby to disable the detection means.

As a further development, the enabling means may be adapted to enable the detection means for a first predetermined time period after the generating means has ceased generating the atomic cloud and when the atomic cloud no longer emits inherent radiation and for a further predetermined later time period when the concentration of the atomic cloud has decayed to substantially zero; the apparatus also including a processing means for subtracting the output of the detection means during the further time period from that during the first time period. By this means, background radiation, for example due to reflections, may be eliminated.

The apparatus may further include source means for exciting the unknown substance such that it emits source radiation characteristic of its component elements. Such a source means may also comprise a glow discharge lamp of the known type or in accordance with the first aspect of the invention.

Focussing means may be provided for focussing radiation emitted by the unknown substance on the atomic cloud generated by the generating means and for focussing radiation emitted by the atomic cloud on the detection means. Such focussing means may comprise optical lenses, of glass, quartz, lithium fluoride or any other suitable material.

As the excited atoms re-radiate radiation having different frequencies, a filter means may be provided in the radiation path between the generating means and the detection means for allowing only radiation in a predetermined frequency band to pass through to the detection means.

As a preferred feature, the generating means, the enabling means and the detection means may be operable in a pulsed repetitive manner, the apparatus including averaging means for averaging the output of the detection means.

A recording means may also be provided for recording the output of the detection means.

Further according to the second aspect of the invention there is provided a method for spectroscopically determining the presence of a particular element in a substance of unknown composition including generating by cathodic sputtering an atomic cloud of the particular element;

ceasing to generate the atomic cloud;

allowing the inherent radiation emitted by the atomic cloud to decay to substantially zero;

irradiating the atomic cloud with radiation emitted from the substance that is characteristic of its component elements such that selected components of the radiation are absorbed by the atoms of the atomic cloud and the atoms of the atomic cloud re-radiate characteristic radiation; and detecting the amount of re-radiated radiation when the inherent radiation of the atomic cloud has decayed.

Re-radiation of the atoms of the atomic cloud of the resonant type may be detected.

The amount of re-radiated radiation may be detected by detecting the amount of radiation occurring when the atomic cloud has a substantial concentration of atoms; allowing the concentration of atoms to decay to substantially zero; determining the amount of background radiation occurring when the concentration of atoms has so decayed; and subtracting this amount of background radiation from the amount of radiation occurring when the atomic cloud has a substantial concentration of atoms.

As the radiation emitted by the atomic cloud is dependent on the intensity of primary radiation from the substance which it experiences, this intensity in turn being dependent on the concentration of the reference element in the substance, the detection means may be calibrated, using a substance of known composition to determine the concentration of the reference element in the unknown substance.

As indicated earlier, the radiation may be emitted from the unknown substance by cathodic sputtering of a cathode composed of the unknown substance.

Further, the atomic cloud of the particular element may be repetitively generated; the amount of re-radiated radiation may be repetitively detected; and the average amount of re-radiated radiation may be determined.

The apparatus may further include a plurality of discharge lamps and/or detection and enabling means, such that the presence of a plurality of elements in the unknown substance may be determined sequentially or simultaneously. Thus, a plurality of discharge lamps, each having its own detection and enabling means may be arranged serially along the optical path of the radiation emitted by the substance. Alternatively, only one discharge lamp may be provided, the cathode of which is composed of several elements, or the discharge lamp may have a plurality of cathodes being simultaneously or sequentially utilised; the apparatus then having a suitable energising means for sequentially energising the cathodes.

BRIEF DESCRIPTION OF THE DRAWINGS

The invention will now be described by way of examples with reference to the accompanying drawings, in which:

Referring to FIGS. 1, 2 and 3, apparatus for spectroscopically analysing a substance of unknown composition is shown generally by reference numeral 10. The embodiment shown in FIG. 1 will first be considered in detail, however, like components in FIGS. 2 and 3 will be given like reference numerals.

Figure 1:
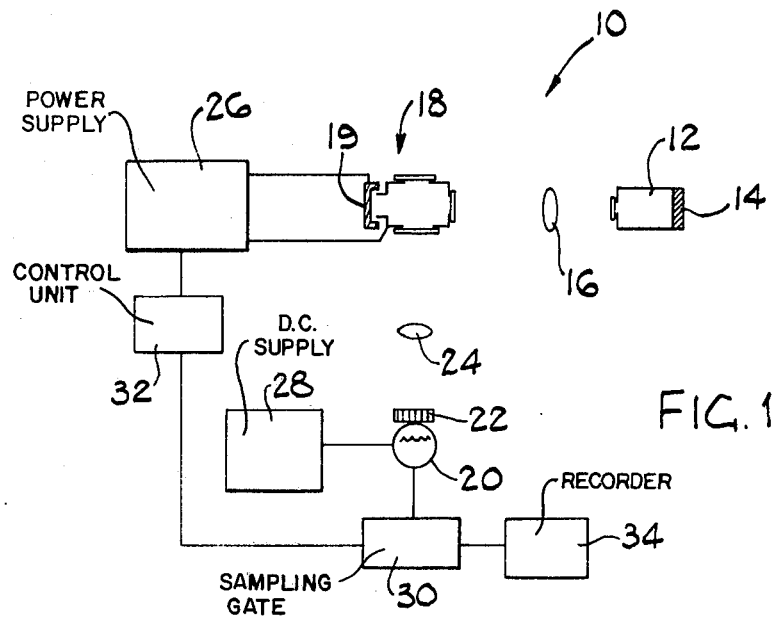
FIGS. 1, 2 and 3 each show schematically an embodiment of apparatus for spectroscopically analysing a substance.

The apparatus 10 of FIG. 1 includes a source glow discharge lamp 12 (discussed in further detail hereinafter, with reference to FIG. 6) for exciting a sample 14 of an unknown substance to emit primary radiation characteristic of the component elements of the sample. Primary radiation emitted from the source lamp 12 is focussed by a quartz lens 16 into a resonance glow discharge lamp 18. The resonance lamp 18 generates an atomic cloud from a reference sample 19 of a particular element, the concentration whereof in the sample 14 is to be determined. The resonance lamp 18 is also discussed hereinafter with reference to FIG. 5.

Resonance fluorescence emitted by the atomic cloud of the resonance lamp 18 is focussed onto a photomultiplier tube 20, via an interference filter 22, by a further quartz lens 24. As shown, the optical axes of the primary radiation from the source lamp 12 and the resonance fluoresence from the resonance lamp 18, are transverse to one another.

The resonance lamp 18 generates the atomic cloud of the particular element from the reference sample 19 by cathodic sputtering, and is supplied with power from a pulsed electrical power supply 26. The photomultiplier tube 20 is supplied from a D.C. supply 28, and its output is sampled by an electronic sampling gate 30. The resonance lamp power supply 26 and the sampling gate 30, are controlled by a control unit 32, such that the photomultiplier tube 20 is enabled and its output is sampled when the resonance lamp 18 is not excited, i.e. out of phase with one another The sampled output of the photomultiplier tube 20 is integrated and recorded by a recorder 34.

In use, the source lamp 12 is electrically excited, causing atoms of the sample 14 to be excited, the atoms then emitting characteristic primary or source radiation. This primary radiation is focussed onto the atomic cloud generated by the resonance lamp 18. If the sample 14 contains atoms of the same element as that of the atomic cloud, i.e. if the sample 14 emits primary radiation characteristic of the atoms of the cloud, some of the atoms of the cloud will be excited by the primary radiation and will fluoresce. A certain proportion of this fluorescent radiation will be of the resonance type, i.e. the atoms will be excited from their ground state to a first excited level and will then return to their ground state emitting radiation of the same frequency as that which excited them. As the two optical axes referred to earlier are transverse to one another, only the fluorescent radiation, a certain amount of reflected primary radiation, and a certain amount of the inherent radiation of the resonance lamp 18 is focussed on the photomultiplier tube 20.

In order to eliminate all radiation except that at the resonance frequency, i.e. to eliminate the other spectral lines of the particular reference element and to minimise background noise, the narrow bandwidth interference filter 22 is interposed between the photomultiplier tube 20 and the resonance lamp 18.

In order to eliminate the inherent radiation from the resonance lamp 18, the lamp 18 is pulsed, generating the atomic cloud by cathodic sputtering. The lamp 18 is then de-energised, and as discussed earlier, as the gas pressure in the resonance lamp 18 is at a suitable value the inherent radiation decays much more rapidly than the atomic cloud concentration. The relevant wave forms are illustrated by graphs 44.1, 44.2 and 44.3 in FIG. 4.

Figure 4:
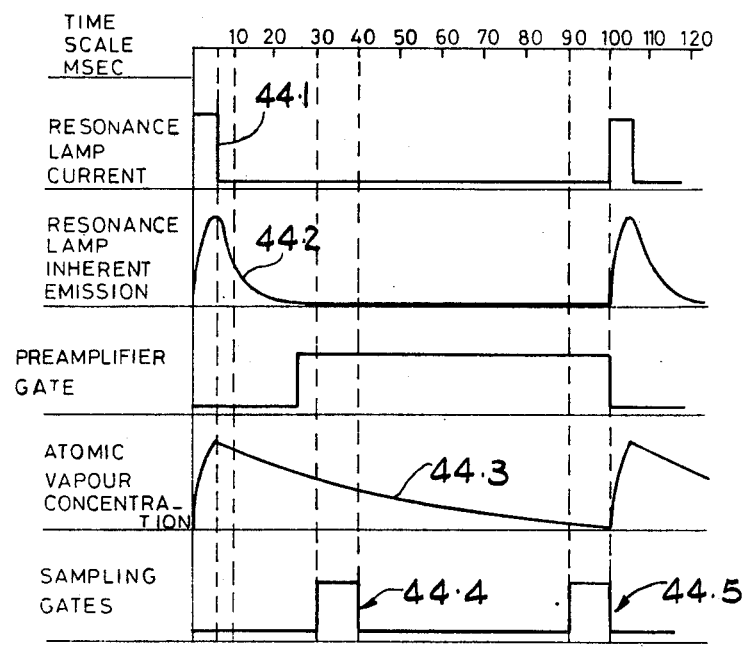
FIG. 4 shows the wave forms of the embodiment of FIG. 3.

When the inherent radiation of the resonance lamp 18 has decayed to substantially zero, but the atomic cloud is still fluorescing, the output of the photomultiplier tube 20 is sampled, as indicated at 44.4 in FIG. 4.

This process is repeated, and the pulses from the sampling gate 30 integrated and averaged by the recorder 34. The output of the recorder 34 is then an indication of the concentration of the reference element in the sample 14.

In order to get an absolute indication of the concentration, the apparatus 10 is first calibrated against a substance of known concentration.

Figure 2:
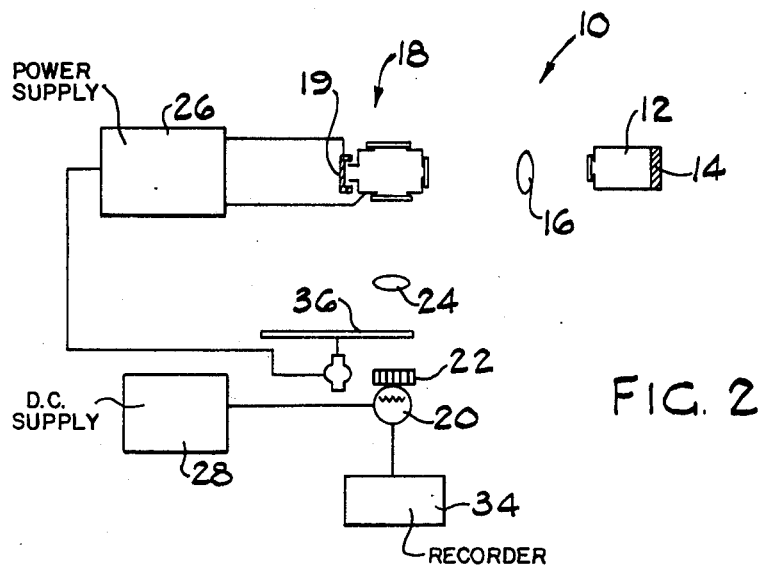

The apparatus 10 of FIG. 2 is similar to that of FIG. 1, except that instead of sampling the output of the resonance lamp 18 with an electronic gate, a mechanical shutter/chopper 36 is utilised to enable and disable the photomultiplier tube 20. Suitable contacts are provided on the chopper 36 for controlling the pulse power supply 26.

Figure 3:
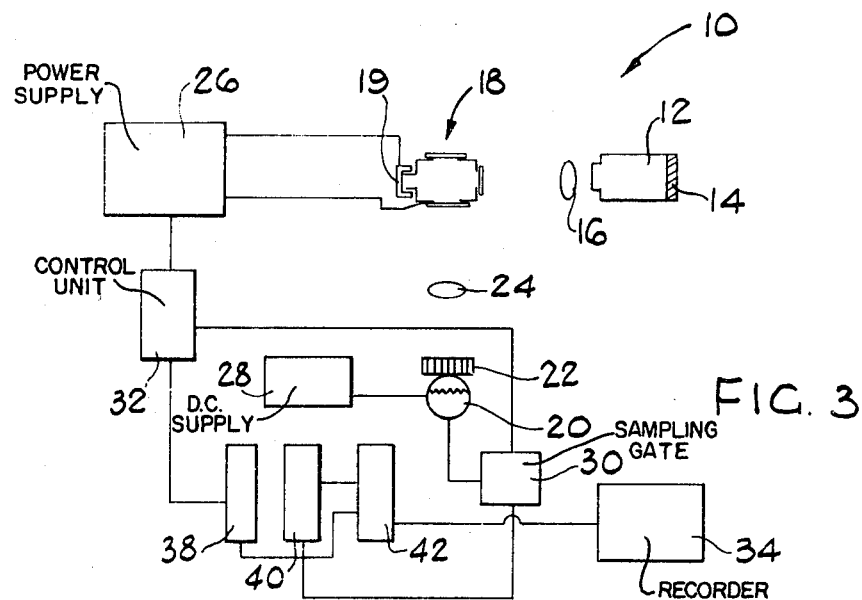

The further embodiment of FIG. 3 also has an electronic gate 30 and is adapted to also eliminate the reflections referred to earlier, thus further minimising the background noise and enhancing the detection ability of the apparatus 10. With this embodiment, the output of the photomultiplier tube 20 is also sampled when the concentration of the atomic cloud has decayed to virtually zero, i.e. the fluorescent radiation has ceased. The output of the gate 30 is fed to an amplifier/shaper 40 and then to a differential gated amplifier 42 which is gated by a dual gate generator 38 so that the second pulse (reflected background), is inverted. By this means, the recorder 34 differentially integrates the two signals, thereby eliminating the reflected background. This further sampling is indicated at 44.5 in FIG. 4.

Figure 5:
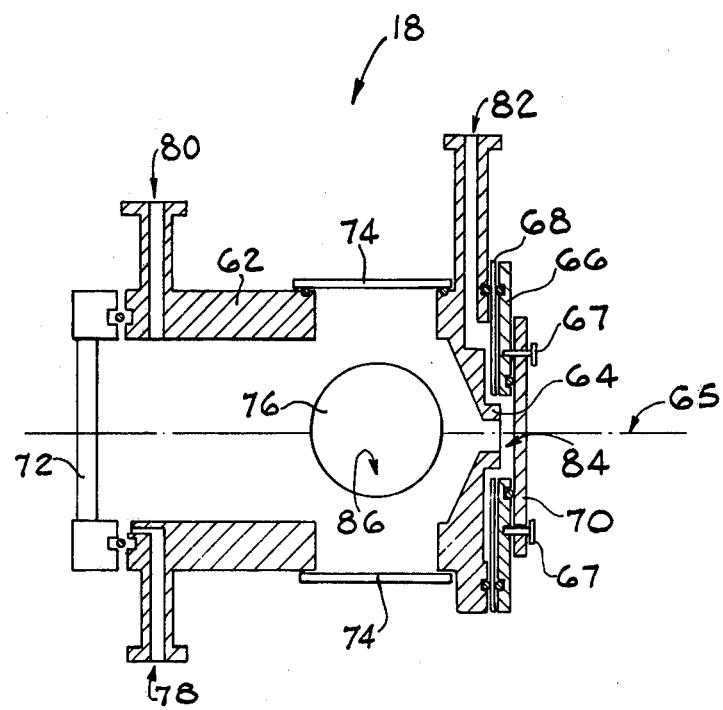
FIG. 5 shows schematically a glow discharge resonance lamp used in the embodiments of FIGS. 1, 2 and 3.

The resonance lamp 18 is now described, with reference to FIG. 5.

The lamp 18 includes an anode block 62 which defines a housing and which has at one end a tubular anode 64 of about 2cm long having an axis 65. An annular cathode block 66 is secured to the anode block 62 and is insulated from it by a Teflon separator 68. A disc 70, forming the reference sample 19, is replaceably secured to the cathode block 66 by screws 67. The disc 70 is in electrical contact with the cathode block 66 and forms part of the cathode. The separation between the anode 64 and the disc 70 is in the region of 0.02mm – 1.

At the end remote from the anode 64, a quartz window 72 is provided in the anode block 62, with the axis 65 of the anode 64 passing through it. Further quartz windows 74 and 76 are provided in the anode block 62 on axes that are mutually perpendicular to one another and to the axis 65. The resonance lamp 18 is located such that primary radiation from the source lamp 12 enters through its window 72 to irradiate the atomic cloud generated within and cause fluorescence thereof. This fluorescence is radiated in all directions and is emitted through the windows 74 and 76 along optical axes perpendicular to the anode axis 65. The lens 24, the filter 22 and the photomultiplier tube 20 are located on the optical axis passing through the windows 74.

An inlet opening 78, and two outlet openings 80 and 82 are provided, such that an inert gas, such as argon, may be introduced into the lamp 18 and be exhausted to create a pressure gradient in the region 84 between the anode 64 and the disc 70, in a known manner.

In use, the lamp 18 is suitably pressurized, such that the rate constant k(P) is a desired value and the anode 64 and the cathodes 66, 70 are energised from the source 26, thereby generating an atomic cloud of the reference element by cathodic sputtering. Due to the short length of the anode 64, the cloud extends to the region 86 between the windows 74 and 76.

The lamp 18 may also be used in absorption spectroscopy, radiation from the source lamp 12 passing through the atomic cloud, via the windows 74.

Figure 6:
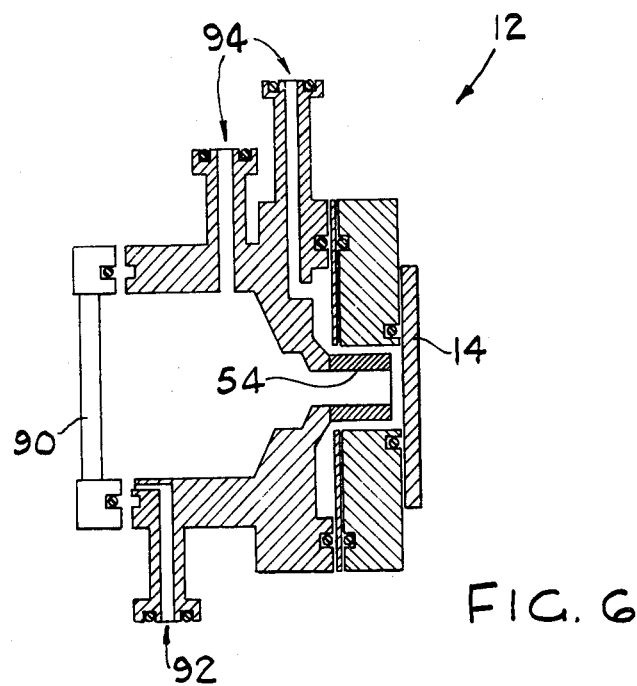
FIG. 6 shows a schematic cross-sectional view of a glow discharge source lamp used in the embodiments of FIGS. 1, 2 and 3.

Referring to FIG. 6 a hollow-anode or glow discharge lamp 12 is shown. The lamp 12 has a hollow anode 54 spaced about 0.02 mm from a transverse planar cathode 14 formed from the unknown substance. It also has only one quartz window 90 and an inlet opening 92 and outlet openings 94 so that it may be pressurized with argon.

Figure 7:
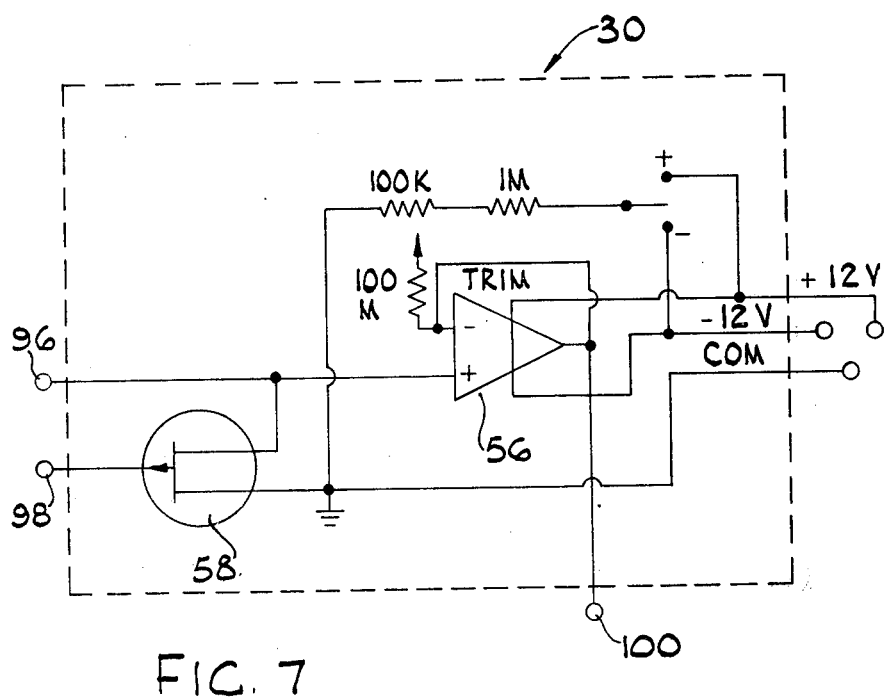
FIG. 7 is a circuit diagram of an electronic gate used in the embodiments of FIGS. 1 and 3.

Referring finally to FIG. 7, the sampling gate 30 is shown. The sampling gate 30 has an operational amplifier 56, with an input FET gate 58. The FET gate 58 is connected between ground and the input 96 to the sampling gate 30. The FET gate 58 is controlled from the control unit 32 via a control input 98 to either ground the input 96 or to connect it to the operational amplifier 56, the output 100 of which is connected to the recorder 34 or the amplifier/shaper 40.

By means of the apparatus as shown in FIG. 3, it has been possible to detect from ±1ppm to ±20% copper in aluminium. Accordingly, by means of the apparatus and the method of the invention, unknown samples may easily, cheaply and accurately by analysed by spectrographic techniques.

It will further be appreciated that the apparatus 10 shown in FIGS. 1, 2 and 3 may easily be modified so that the concentration of more than one element in the unknown substance may be determined. For example, the cathode disc 70 of the resonance lamp 18 may be an alloy of two elements. An atomic cloud will then be generated having atoms of both elements, resonant radiation being emitted by atoms of both elements. A further interference filter, photomultiplier tube, sampling gate and recorder may be provided, with the interference filter and photomultiplier tube being disposed on the optical axis passing through the windows 76. The concentration of both reference elements in the unknown substance can then be determined simultaneously.

Alternatively, the resonance lamp 18 may have a further anode and cathode, the anode being disposed on the axis passing through the windows 76. This further cathode is then of a different reference element. The two sets of anodes and cathodes are then sequentially energised, the power supply being suitably modified. The concentrations of the two reference elements in the unknown substance are then sequentially determined by the same photomultiplier tube.

As a still further alternative, the primary radiation may be directed through the windows 74 the resonance radiation being emitted through either the window 72 or the windows 76. A further resonance lamp may then be provided in the path of the primary radiation that has passed through the first resonance lamp, the resonance lamps having different reference elements. This further resonance lamp will have its own associated photomultiplier tube, so that the concentrations of the reference elements are simultaneously determined. Naturally, further resonance lamps may be serially arranged to determine the concentrations of further elements.

I claim:

1. An apparatus for spectroscopically determining the presence of a particular element in a substance of unknown composition comprising
    generating means for generating by cathodic sputtering an atomic cloud of the particular element,
    means for controlling said generating means to cease atomic cloud generation to allow the inherent radiation emitted by the cloud to decay to substantially zero,
    means for irradiating the atomic cloud with radiation emitted from a substance that is characteristic of its component elements such that selected components of the radiation are absorbed by the atoms of the atomic cloud and the atoms of the atomic cloud re-radiate characteristic radiation,
    means for detecting the amount of re-radiated characteristic radiation emitted by the atomic cloud,
    enabling means enabling the detection means for a first predetermined period of time after the generating means has ceased generating the cloud and the atomic cloud no longer emits inherent radiation to allow detecting of the amount of re-radiated radiation when the inherent radiation of the atomic cloud has decayed, said enabling means enabling said detection means for a further predetermined later time period when the concentration of the atomic cloud has decayed to substantially zero, and a processing means for subtracting the output of the detection means during the later time period from the output for the first time period.

2. An apparatus as claimed in claim 1, in which the generating means comprises a glow discharge lamp.

3. An apparatus as claimed in claim 1, in which the enabling means comprises a mechanical shutter that is displaceable in and out of the optical path between the generating means and the detection means.

4. An apparatus as claimed in claim 1, in which the detection means is electrically operable and the enabling means is also electrically operable.

5. An apparatus as claimed in claim 4, in which the enabling means is adapted to electrically ground the output of the detection means thereby to disable the detection means.

6. An apparatus as claimed in claim 1, which includes source means for exciting the unknown substance such that it emits source radiation characteristic of its component elements.

7. An apparatus as claimed in claim 6, which includes focussing means for focussing radiation emitted by the unknown substance on the atomic cloud generated by the generating means and for focussing radiation emitted by the atomic cloud on the detection means.

8. An apparatus as claimed in claim 1, which includes a filter means provided in the radiation path between the generating means and the detection means for allowing only radiation in a predetermined frequency band to pass through to the detection means.

9. An apparatus as claimed in claim 1, in which the generating means, the enabling means and the detection means are operable in a pulsed repetitive manner and the apparatus includes averaging means for averaging the output of the detection means.

10. An apparatus as claimed in claim 1, which includes a recording means for recording the output of the detection means.

11. A method for spectroscopically determining the presence of a particular element in a substance of unknown composition including
- generating by cathodic sputtering an atomic cloud of the particular element;
- ceasing to generate the atomic cloud;
- allowing the inherent radiation emitted by the atomic cloud to decay to substantially zero;
- irradiating the atomic cloud with radiation emitted from the substance that is characteristic of its component elements such that selected components of the radiation are absorbed by the atoms of the atomic cloud and the atoms of the atomic cloud re-radiate characteristic radiation; and
- detecting the amount of re-radiated radiation when the inherent radiation of the atomic cloud has decayed, said re-radiated radiation being detected by
- detecting the amount of radiation occurring when the atomic cloud has a substantial concentration of atoms;
- allowing the concentration of atoms to decay to substantially zero;
- determining the amount of background radiation occurring when the concentration of atoms has so decayed; and
- subtracting this amount of background radiation from the amount of radiation occurring when the atomic cloud has a substantial concentration of atoms.

12. A method as claimed in claim 11, in which re-radiation of the atoms of the atomic cloud of the resonant type is detected.

13. A method as claimed in claim 11, in which the concentration of the particular element in the unknown substance is determined by first calibrating the amount of radiation determined by means of a substance of known composition.

14. A method as claimed in claim 11, in which radiation is emitted from the unknown substance by cathodic sputtering of a cathode composed of the unknown substance.

15. A method as claimed in claim 1, in which
- the atomic cloud of the particular element is repetitively generated;
- the amount of re-radiated radiation is repetitively detected; and
- the average amount of re-radiated radiation is determined.

* * * * *